United States Patent [19]

Friebe et al.

[11] 4,427,680
[45] Jan. 24, 1984

[54] 1,2-DIHYDROQUINOLINES CONNECTED VIA AN OXYALKYL GROUP WITH A PIPERIDINE RING AND HAVING ANTI-ALLERGIC ACTION

[75] Inventors: Walter-Gunar Friebe, Darmstadt; Werner Winter, Heppenheim; Max Thiel; Androniki Roesch, both of Mannheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 346,790

[22] Filed: Feb. 8, 1982

Related U.S. Application Data

[62] Division of Ser. No. 104,205, Dec. 17, 1979, Pat. No. 4,330,549.

[30] Foreign Application Priority Data

Jan. 15, 1979 [DE] Fed. Rep. of Germany ....... 2901336

[51] Int. Cl.³ .................... A61K 31/47; C07D 215/22; C07D 401/12
[52] U.S. Cl. ...................................... 424/258; 546/157
[58] Field of Search ................. 546/157, 158; 424/258

[56] References Cited

U.S. PATENT DOCUMENTS

| 3,340,266 | 9/1967 | Howe et al. | 546/157 |
| 4,029,801 | 6/1977 | Cavalla et al. | 424/267 |
| 4,210,753 | 7/1980 | Tominaga et al. | 544/128 |
| 4,264,599 | 4/1981 | Eichenberger et al. | 424/250 |
| 4,288,442 | 9/1981 | Friebe et al. | 424/267 |
| 4,330,549 | 5/1982 | Friebe et al. | 424/267 |

FOREIGN PATENT DOCUMENTS

| 49-101387 | 9/1974 | Japan | 546/158 |
| 53-9777 | 1/1978 | Japan | 424/258 |
| 56-43280 | 4/1981 | Japan | 424/258 |
| 57-18674 | 1/1982 | Japan | 424/258 |
| 57-35588 | 2/1982 | Japan | 424/258 |
| 2063869 | 6/1981 | United Kingdom | 424/258 |

*Primary Examiner*—Diana G. Rivers
*Attorney, Agent, or Firm*—Sprung, Horn, Kramer & Woods

[57] ABSTRACT

The present invention provides aryl ether derivatives of the general formula:

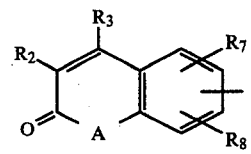

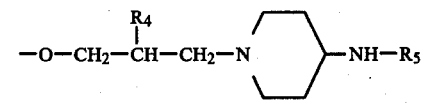

wherein A is an oxygen atom or the group $>N-R_1$, $R_1$ being a hydrogen atom or a lower alkyl radical, $R_2$ and $R_3$, which can be the same or different, are hydrogen atoms or lower alkyl radicals, $R_4$ is a hydrogen atom or a hydroxyl group, $R_5$ is a hydrogen atom or an acyl radical, $R_7$ is a hydrogen atom, a lower alkyl radical or a lower alkanoyl radical and $R_8$ is a hydrogen atom, a lower alkyl radical, a lower alkoxy radical or a hydroxyl group; and the pharmacologically acceptable salts thereof.

The present invention also provides a process for the preparation of these compounds and pharmaceutical compositions containing them. It is also concerned with the use of these compounds for combating allergic diseases.

5 Claims, No Drawings

1,2-DIHYDROQUINOLINES CONNECTED VIA AN OXYALKYL GROUP WITH A PIPERIDINE RING AND HAVING ANTI-ALLERGIC ACTION

This is a division of Application Ser. No. 104,205, filed Dec. 17, 1979 now U.S. Pat. No. 4,330,549.

The present invention is concerned with new aryl ether derivatives, with the preparation thereof, with the use thereof and with pharmaceutical compositions containing them.

The new aryl ether derivatives, according to the present invention are compounds of the general formula:

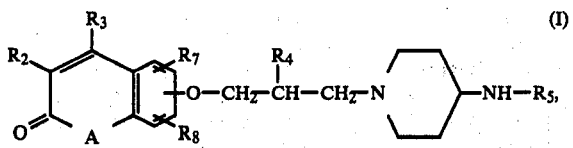

wherein A is an oxygen atom or the group $>N-R_1$, $R_1$ being a hydrogen atom or a lower alkyl radical, $R_2$ and $R_3$, which can be the same or different, are hydrogen atoms or lower alkyl radicals, $R_4$ is a hydrogen atom or a hydroxyl group, $R_5$ is a hydrogen atom or an acyl radical, $R_7$ is a hydrogen atom or a lower alkyl or lower alkanoyl radical and $R_8$ is a hydrogen atom, a lower alkyl radical, a lower alkoxy radical or a hydroxyl group; and the pharmacologically acceptable salts thereof.

The new compounds according to the present invention are useful for the treatment of allergic diseases.

The lower alkyl radicals of the substituents $R_1$, $R_2$, $R_3$, $R_7$ and $R_8$ can be straight or branched chained and contain up to 6 and preferably up to 4 carbon atoms.

A lower alkoxy radical of the substituent $R_8$ can contain up to 6 and preferably up to 4 carbon atoms. A lower alkanoyl radical of the substituent $R_7$ contains up to 6 carbon atoms, the acetyl radical being especially preferred.

The acyl radicals of the substituent $R_5$ can be lower alkanoyl radicals, for example the acetyl radical, which are optionally substituted one or more times by halogen, by aryl, for example phenyl, or by hetaryl, for example benzthiazole derivatives; lower alkenoyl radicals, which can be substituted by aryl optionally carrying one or more substituents, for example an optionally substituted cinnamoyl radical; or carbocyclic- as well as heterocyclic-aroyl radicals, which can optionally be substituted by halogen, hydroxyl, lower alkyl, lower alkoxy, lower alkoxycarbonyl, lower acyloxy, carboxyl, nitro, amino, nitrile, trifluoromethyl, carbamoyl or benzyl. The lower alkyl radicals in the said groups contain up to 6 and preferably up to 4 carbon atoms.

Heterocyclic aroyl radicals can contain one or more hetero atoms, preferred radicals being, for example the furancarbonyl, thiophenecarbonyl and the pyridinecarbonyl radicals. Carbocyclic aroyl radicals include, for example, the benzoyl radical.

Furthermore, $R_5$ can represent the acidic residue of a cycloalkylcarboxylic acid, the cycloalkyl moiety of which is preferably a cyclopropyl, cyclobutyl, cyclopentyl, cyclohexyl or cycloheptyl radical.

Furthermore, the acyl radicals are also to be understood to include acidic residues of sulphonic acids, for example of benzenesulphonic acid and methanesulphonic acid.

Halogen atoms are to be understood to be fluorine, chlorine and bromine.

Apart from the compounds mentioned hereinafter in the specific examples, the present invention also includes, in particular, all compounds which display every possible combination of the substituents mentioned in the specific examples.

Published German Patent Applications Nos. 19 32 384 and 21 23 924 describe piperazine derivatives which are connected via an oxypropyl group to a 2-oxo-1,2-dihydroquinoline or to a coumarin residue; the quinoline derivatives having an outstanding coronary blood vessel dilating action. We have now found that quinolines and coumarins which are connected via an oxyalkyl group with a piperidine ring display an outstanding antiallergic action, as can be demonstrated in the pharmacological test of passive cutaneous anaphylaxis (PCA test) in vivo in rats. Thus, we have found that, in the case of the commercially-available product diethylcarbamazine (1-diethylcarbamazoyl-4-methyl-piperazine), about 40 times more substance must be used than of the compound 7-[3-(4-benzamido-piperidino)-propoxy]-3,4-dimethylcoumarin in order to achieve a comparable inhibition of the passive cutaneous anaphylactoid reaction. Furthermore, the new compounds according to the present invention display a strong anti-histamine effect. Therefore, the compounds of general formula (I) according to the present invention can be employed especially advantageously for combating allergic diseases, for example allergic asthma, hay fever and urticaria.

The new compounds of general formula (I) can be further worked up in various ways to give substances which also display pharmacological effectiveness and especially anti-allergic or anti-hypertensive effectiveness. Therefore, they are also valuable intermediates for the preparation of pharmacologically effective materials.

The process according to the present invention for the preparation of the compounds of general formula (I) is characterized in that, in per se known manner, a compound of the general formula:

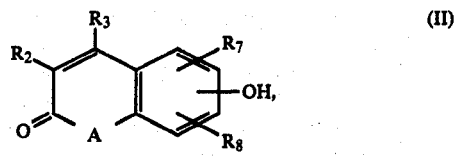

wherein A, $R_2$, $R_3$, $R_7$ and $R_8$ have the above-given meanings, is reacted with a compound of the general formula:

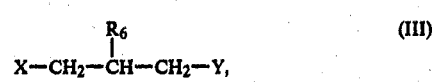

wherein X and Y are reactive residues and $R_6$ is a hydrogen atom or a hydroxyl group or, together with Y, can also represent an oxygen atom, and with a compound of the general formula:

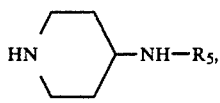

wherein $R_5$ has the same meaning as above, whereafter, if desired, the group $R_5$ is converted by known processes into a different group $R_5$; when $R_1$ is a hydrogen atom, the product obtained is, if desired, subsequently N-alkylated and the product obtained is, if desired, converted into a pharmacologically acceptable salt.

Thus, for example, a compound of general formula (I) with a particular substituent $R_5$ can be converted by saponification and subsequent acylation with a compound of the general formula $R_5$—Z, wherein Z is a reactive residue and $R_5$ is a different substituent of the above-given definition, into a compound of general formula (I) with a different substituent $R_5$. Furthermore, in per se known manner, a compound of general formula (I) in which the substituent $R_5$ contains a nitro group can be reduced to give a compound of general formula (I) with an amino group in the $R_5$ substituent.

The reactive residues X and Y of the compounds of general formula (III) can be all conventional groups which can be displaced nucleophilically, chlorine and bromine atoms, as well as mesyloxy and tosyloxy radicals, being especially preferred.

Reactive residues Z can be all residues which are used in peptide chemistry for the activation of carboxylic acids, for example, halogen atoms, the azido group and alkoxy, aryloxy and acyloxy radicals.

The process according to the present invention is preferably carried out by first condensing compounds of general formula (III) with compounds of general formula (II), the intermediate reaction product obtained being isolated. This intermediate is then reacted with a compound of general formula (IV). The first mentioned reaction is preferably carried out in an alkaline medium in an appropriate solvent, for example a lower alcohol, such as ethanol or isopropanol, in the presence of a sodium alcoholate, but tetrahydrofuran, methoxyethanol, ethoxyethanol, dimethylformamide, dimethyl sulphoxide or hexametapol can also be used, in which case the base used can also be an alkali metal and alkaline earth metal hydroxide or hydride.

The reaction of the above-mentioned intermediate with a compound of general formula (IV) can be carried out in the above-mentioned solvents and, as bases, there can also be used tertiary amines, such as triethylamine, a Hünig base, a strongly basic ion exchanger or an excess of the compound of general formula (IV).

According to another variant, a compound of the general formula (III) is first reacted with a compound of general formula (IV). Subsequently, the reaction mixture obtained is reacted with a compound of the general formula (II) to give the desired end product of general formula (I). The starting reaction takes place in the above-mentioned solvents, advantageously with the addition of a tertiary amine, for example triethylamine, a Hünig base or of a strongly basic ion exchanger but also, for example, in the presence of potassium tert.-butoxide in dimethyl sulphoxide.

A subsequnet conversion of the group $R_5$ in compounds of general formula (I) into a different group $R_5$ can be carried out, for example, as the exchange of an acyl radical $R_5$ for a different radical $R_5$. For this purpose, compounds of general formula (I) are first saponified in an acidic or alkaline medium and the intermediate obtained is then acylated in the presence of an acid-binding agent by means of known methods.

The above-mentioned intermediates of general formula (I), in which $R_5$ is a hydrogen atom, can, however, also be prepared by reacting a compound of general formula (II) with a compound of general formula (III) and 4-oximinopiperidine, the condensation product obtained being subsequently reduced or hydrogenated.

Furthermore, in compounds of general formula (I), in which the acyl radical $R_5$ contains a nitro group, the nitro group can be converted by known methods into an amino group, for example by catalytic hydrogenation.

Starting compounds of general formulae (II), (III) and (IV) are known from the literature and can be prepared by processes analogous to those known from the literature.

The pharmacologically acceptable salts can be obtained in the usual manner, for example, by neutralizing the compounds of general formula (I) with non-toxic inorganic or organic acids, for example, hydrochloric acid, sulphuric acid, phosphoric acid, hydrobromic acid, acetic acid, lactic acid, citric acid, malic acid, salicylic acid, malonic acid, maleic acid or succinic acid.

For the preparation of pharmaceutical compositions, the compounds of general formula (I) are mixed in per se known manner with appropriate pharmaceutical carrier substances and aromatic, flavoring and coloring materials and, for example, formed into tablets or dragees or, with the addition of appropriate adjuvants, suspended or dissolved in water or in an oil, for example olive oil.

The compounds of general formula (I) can be administered orally or parenterally in liquid or solid form. As injection medium, it is preferable to use water which contains the stabilizing agents, solubilizing agents and/or buffers conventional in injection solutions. Additives of this type include, for example, tartrate and borate buffers, ethanol, dimethyl sulphoxide, complex forming agents (such as ethylenediamine-tetraacetic acid), high molecular weight polymers (such as liquid polyethylene oxide) for viscosity regulation and polyethylene derivatives of sorbitol anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavoring and/or sweetening agents.

For external use, the compounds (I) according to the present invention can also be employed in the form of powders and salves, for which purpose they are mixed, for example, with powdered, physiologically acceptable dilution agents or with conventional salve bases.

The dosage administered depends upon the age, state of health and the weight of the recipient, the extent of the disease, the nature of further treatments possibly carried out simultaneously, the frequency of the treatment and the nature of the desired effect. Usually, the daily dosage of the active compounds is 0.1 to 50 mg./kg. of body weight. Normally, 0.5 to 40 and preferably 1.0 to 20 mg./kg./day are effective in one or more administrations per day in order to achieve the desired results.

Apart from the compounds mentioned in the following examples, also preferred according to the present invention are the following compounds:

6-[3-(4-benzamido-piperidino)-propoxy]-1-n-butyl-4-methyl-2-oxo-1,2-dihydroquinoline; and 6-[3-(4-benzamido-piperidino)-propoxy]-4-methyl-1-(2-methylbutyl)-2-oxo-1,2-dihydroquinoline.

The following examples are given for the purpose of illustrating the present invention:

EXAMPLE 1

7-[3-(4-Benzamido-piperidino)-propoxy]-3,4-dimethyl-coumarin

A mixture of 9.34 g. (0.03 mol) 7-(3-bromopropoxy)-3,4-dimethyl-coumarin, 6.13 g. (0.03 mol) 4-benzamido-piperidine, 12.43 g. (0.09 mol) triethylamine and 100 ml. tetrahydrofuran is heated under reflux for 6 hours. The reaction mixture is then evaporated in a vacuum and the residue is taken up in water, extracted with methylene chloride and the extract evaporated. After recrystallization of the residue from methanol, there are obtained 6.5 g. 7-[3-(4-benzamido-piperidino)-propoxy]-3,4-dimethyl-coumarin (50% of theory); m.p. 201°–203° C.

EXAMPLE 2

In a manner analogous to that described in Example 1, there are obtained:

| designation | Yield % | m.p. °C. (solvent) |
|---|---|---|
| (a) 3,4-Dimethyl-7-{3-[4-(4-fluoro-benzamido)-piperidino]-propoxy}-coumarin from 7-(3-bromopropoxy)-3,4-dimethyl-coumarin and 4-(4-fluorobenz-amido)-piperidine | 59 | hydrochloride 268–270 (isopropanol) |
| (b) 3,4-Dimethyl-7-{3-[4-(4-methoxy-benzamido)-piperidino]-propoxy}-coumarin from 7-(3-bromopropoxy)-3,4-dimethyl-coumarin and 4-(4-methoxy-benzamido)-piperidine | 43 | hydrochloride 266–268 (isopropanol) |
| (c) 3,4-Dimethyl-7-{3-[4-(4-methyl-benzamido)-piperidino]-propoxy}-coumarin from 7-(3-bromopropoxy)-3,4-dimethyl-coumarin and 4-(4-methyl-benzamido)-piperidine | 38 | hydrochloride 272–274 (isopropanol) |
| (d) 7-{3-[4-(4-t.-Butyl-benzamido)-piperidino]-propoxy}-3,4-dimethyl-coumarin from 7-(3-bromopropoxy)-3,4-dimethyl-coumarin and 4-(4-t.-butyl-benzamido)-piperidine | 61 | hydrochloride 295–296 (isopropanol) |
| (e) 7-[3-(4-Acetamido-piperidino)-propoxy]-3,4-dimethyl-coumarin from 7-(3-bromopropoxy)-3,4-dimethyl-coumarin and 4-acetamido-piperidine | 28 | hydrochloride 172–174 (isopropanol) |
| (f) 3,4-Dimethyl-7-[3-(4-phenyl-acetamido-piperidino)-propoxy]-coumarin from 7-(3-Bromopropoxy)-3,4-dimethyl-coumarin and 4-phenylacetamido-piperidine | 49 | 139–140 (ethyl acetate) |
| (g) 3,4-Dimethyl-7-{3-[4-(2-methyl-propionamido)-piperidino]-propoxy}-coumarin from 7-(3-bromopropoxy)-3,4-dimethyl-coumarin and 4-(2-methyl-propionamido)-piperidine | 91 | 176–178 (isopropanol) |
| (h) 7-[3-(4-Cyclohexancarbonamido-piperidino)-propoxy]-3,4-dimethyl-coumarin from 7-(3-bromopropoxy)-3,4-dimethyl-coumarin and 4-cyclohexancarbonamido-piperidine | 36 | 174–177 (isopropanol) |

EXAMPLE 3

7-[3-(4-Benzamido-piperidino)-propoxy]-coumarin 4.65 g. (0.025 mol) 7-Hydroxycoumarin are added to a solution of 0.58 g. (0.025 mol) sodium in 100 ml. isopropanol. The mixture is heated under reflux for 10 minutes, cooled and 7.25 g. (0.025 mol) 3-(4-benzamido-piperidino)-propyl chloride in 25 ml. isopropanol added thereto. After boiling under reflux for 6 hours, the reaction mixture is evaporated in a vacuum and the residue is taken up in methylene chloride, washed with 2N aqueous sodium hydroxide solution and subsequently with water, evaporated and the residue recrystallized from ethanol. There are obtained 8.9 g. (88% of theory) 7-[3-(4-benzamido-piperidino)-propoxy]-coumarin; m.p. 157°–158° C.

EXAMPLE 4

In a manner analogous to that described in Example 3, there are obtained:

| designation | Yield % | m.p. °C. (solvent) |
|---|---|---|
| (a) 6-[3-(4-Benzamido-piperidino)-propoxy]-4-methyl-coumarin from 6-hydroxy-4-methyl-coumarin and 3-(4-benzamido-piperidino)-propyl chloride | 66 | 184–186 (methanol) |
| (b) 7-[3-(4-Benzamido-piperidino)-propoxy]-4-methyl-coumarin from 7-hydroxy-4-methyl-coumarin and 3-(4-benzamido-piperidino)-propyl chloride | 48 | 164–166 (isopropanol) |

EXAMPLE 5

1-(4-Benzamido-piperidino)-3-(3,4-dimethyl-coumarin-7-yloxy)-propan-2-ol

A mixture of 8.1 g. (0.033 mol) 3,4-dimethyl-7-(2,3-epoxypropoxy)-coumarin, 6.73 g. (0.033 mol) 4-benzamidopiperidine and 75 ml. ethanol is heated under reflux for 6 hours and then evaporated. The residue is taken up in ethyl acetate, washed with water, evaporated and recrystallized from ethyl acetate. There are obtained 2.8 g. (26% of theory) 1-(4-benzamido-piperidino)-3-(3,4-dimethyl-coumarin-7-yloxy)-propan-2-ol; m.p. 178°–180° C.

EXAMPLE 6

7-{3-[4-(4-Chlorobenzamido)-piperidino]-propoxy}-3,4-dimethylcoumarin

A solution of 3.85 g. (0.022 mol) 4-chlorobenzoyl chloride in 25 ml. tetrahydrofuran is added dropwise to a mixture of 6.6 g. (0.02 mol) 7-[3-(4-amino-piperidino)-propoxy]-3,4-dimethylcoumarin, 100 ml. 2N aqueous sodium hydroxide solution and 75 ml. tetrahydrofuran.

The reaction mixture is stirred for 5 hours at ambient temperature, filtered and the precipitate obtained recrystallized from ethanol. There are obtained 5.5 g. (59% of theory) 7-{3-[4-(4-chlorobenzamido)-piperidino]-propoxy}-3,4-dimethylcoumarin; m.p. 212°–214° C.

The 7-[3-(4-amino-piperidino)-propoxy]-3,4-dimethylcoumarin used as starting material can be obtained in the following manner:

By the reaction of 7-(3-bromopropoxy)-3,4-dimethyl-coumarin with 4-oximino-piperidine hydrochloride in dioxane solution in the presence of a Hunig base, there is obtained 3,4-dimethyl-7-[3-(4-oximino-piperidino)-propoxy]-coumarin (m.p. 198°–200° C.), from which, by catalytic hydrogenation over Raney nickel in ammoniacal methanol, there is obtained 7-[3-(4-amino-piperidino)-propoxy]-3,4-dimethyl-coumarin; m.p. 92°–94° C.

The same coumpound can be obtained, for example, by treating 7-[3-(4-benzamido-piperidino)-propoxy]-3,4-dimethyl-coumarin with an alcoholic solution of potassium hydroxide.

Furthermore, the compound can also be obtained by reacting 4-aminopiperidine with 7-(3-bromopropoxy)-3,4-dimethylcoumarin under reflux in ethanol in the presence of triethylamine.

EXAMPLE 7

In a manner analogous to that described in Example 6, there are obtained:

| designation | Yield % | m.p. °C. (solvent) |
|---|---|---|
| (a) 3,4-Dimethyl-7-{3-[4-(2-hydroxy-benzamido)-piperidino]-propoxy}-coumarin from 7-[3-(4-amino-piperidino)-propoxy]-3,4-dimethyl-coumarin and salicylic acid chloride | 67 | 192–194 (ethyl acetate) |
| (b) 3,4-Dimethyl-7-{3-[4-(thiophene-2-carbonamido)-piperidino]-propoxy-coumarin from 7-[3-(4-amino-piperidino)-propoxy]-3,4-dimethyl-coumarin and thiophene-2-carboxylic acid chloride | 31 | 197–200 (isopropanol) |
| (c) 7-[3-(4-Benzoylsulphonamido-piperidino)-propoxy]-3,4-dimethyl-coumarin from 7-[3-(4-amino-piperidino)-propoxy]-3,4-dimethyl-coumarin and benzene sulphonic acid chloride | 29 | 136–138 (isopropanol) |
| (d) 7-{3-[4-(3,4-Dimethoxy-cinnamoyl-amido)-piperidino]-propoxy}-3,4-dimethyl-coumarin from 7-[3-(4-amino-piperidino)-propoxy]-3,4-dimethyl-coumarin and 3,4-dimethoxy-cinnamic acid chloride | 37 | 195–196 (isopropanol) |
| (e) 7-[3-(4-Cyclopropancarbonylamido-piperidino)-propoxy]-3,4-dimethyl-coumarin from 7-[3-(4-amino-piperidino)-propoxy]-3,4-dimethyl-coumarin and cyclopropane-carboxylic acid chloride | 33 | 190–191 (ethyl acetate) |
| (f) 3,4-Dimethyl-7-{3-[4-(furan-2-carbonamido)-piperidino]-propoxy}-coumarin from 7-[3-(4-amino-piperidino)-propoxy]-3,4-Dimethyl-coumarin and furan-2-carboxylic acid chloride | 40 | 182–183 (methanol) |
| (g) 3,4-Dimethyl-7-{3-[4-(4-nitrobenz-amido)-piperidino]-propoxy}-coumarin from 7-[3-(4-amino-piperidino)-propoxy]-3,4-dimethyl-coumarin and 4-nitro-benzoyl chloride | 62 | 210–212 (methylene chloride) |
| (h) 7-{3-[4-(5-chloro-2-methoxy-benzamido)-piperidino]-propoxy}-3,4-dimethyl-coumarin from 7-[3-(4-amino-piperidino)-propoxy]-3,4-dimethyl-coumarin and 5-chloro-2-methoxy-benzoyl chloride | 69 | 151–152 (isopropanol) |
| (i) 7-{3-[4-(2,3-Dihydro-2-oxo-benzthiazol-3-yl-acetamido)-piperidino]-propoxy}-3,4-dimethyl-coumarin from 7-[3-(4-amino-piperidino)-propoxy]-3,4-dimethyl-coumarin and 2,3-dihydro-2-oxo-benzthiazol-3-yl-acetyl chloride | 58 | 221–222 (methanol) |
| (j) 7-{3-[4-(5-Chloro-2,3-dihydro-2-oxo-benzthiazol-3-yl-acetamido)-piperidino]-propoxy}-3,4-dimethyl coumarin from 7-[3-(4-amino-piperidino)-propoxy]-3,4-dimethyl-coumarin and 5-chloro-2,3-dihydro-2-oxo-benzthiazol-3-yl-acetyl chloride | 51 | 238–240 (methanol) |

EXAMPLE 8

6-[3-(4-Benzamido-piperidino)-propoxy]-4-methyl-2-oxo-1,2-dihydroquinoline 4.9 g. (0.03 mol) 6-Hydroxy-4-methyl-2-oxo-1,2-dihydroquinoline are dissolved in 60 ml. water and 30 ml. 1N aqueous sodium hydroxide solution. The solution is subsequently substantially evaporated and the residue is taken up in 75 ml. dimethylformamide and mixed with 9.8 g. (0.035 mol) 3-(4-benzamido-piperidino)-propyl chloride. After stirring for 4 hours at 100° C., the solvent is removed in a vacuum and the residue taken up in methylene chloride, dried and evaporated. After recrystallization from ethanol, there are obtained 6.8 g. (54% of theory) 6-[3-(4-benzamido-piperidino)-propoxy]-4-methyl-2-oxo-1,2-dihydroquinoline; m.p. 243°–245° C.

EXAMPLE 9

7-[3-(4-Benzamido-piperidino)-propoxy]-4-methyl-2-oxo-1,2-dihydroquinoline

In a manner analogous to that described in Example 8, by the reaction of 7-hydroxy-4-methyl-2-oxo-1,2-dihydroquinoline with 3-(4-benzamido-piperidino)-propyl chloride in methoxyethanol, there is obtained, in a yield of 46% of theory, 7-[3-(4-benzamidopiperidino)-propoxy]-4-methyl-2-oxo-1,2-dihydroquinoline; m.p. 275°–276° C.

EXAMPLE 10

6-[3-(4-Benzamido-piperidino)-propoxy]-1,4-dimethyl-2-oxo-1,2-dihydroquinoline

A solution of 0.8 g. sodium hydroxide in 10 ml. water is added dropwise, under reflux, to a solution of 3.55 g. (0.02 mol) 1,4-dimethyl-6-hydroxy-2-oxo-1,2-dihydroquinoline, 7.0 g. (0.025 mol) 3-(4-benzamidopiperidino)-propyl chloride and 3.0 g. (0.02 mol)

sodium iodide in 10 ml. water and 50 ml. methanol. The reaction mixture is then boiled for 3 hours and evaporated and the residue is taken up in methylene chloride, washed with a dilute aqueous sodium hydroxide solution and evaporated and the residue is recrystallized from isopropanol. There are obtained 4.0 g. (47% of theory) 6-[3-(4-benzamidopiperidino)-propoxy]-1,4-dimethyl-2-oxo-1,2-dihydroquinoline; m.p. 188°–190° C.

EXAMPLE 11

7-[3-(4-Benzamido-piperidino)-propoxy]-1,4-dimethyl-2-oxo-1,2-dihydroquinoline

In a manner analogous to that described in Example 10, by the reaction of 1,4-dimethyl-7-hydroxy-2-oxo-1,2-dihydroquinoline with 3-(4-benzamidopiperidino)-propyl chloride in methoxyethanol, there is obtained, in a yield of 67% of theory, 7-[3-(4-benzamido-piperidino)-propoxy]-1,4-dimethyl-2-oxo-1,2-dihydroquinoline; m.p. 193°–195° C.

(a)
7-[3-(4-Benzamido-piperidino)-propoxy]-1-ethyl-4-methyl-2-oxo-1,2-dihydroquinoline In a manner analogous to that described in Example 11, by the reaction of 1-ethyl-7-hydroxy-4-methyl-2-oxo-1,2-dihydroquinoline with 3-(4-benzamidopiperidino)-propyl chloride, there is obtained, in a yield of 59% of theory, 7-[3-(4-benzamido-piperidino)-propoxy]-1-ethyl-4-methyl-2-oxo-1,2-dihydroquinoline; m.p. 164°–165° C. (after recrystallization from dichloromethane/diethyl ether).

EXAMPLE 12

7-{3-[4-(4-Aminobenzamido)-piperidino]-propoxy}-3,4-dimethyl-coumarin

A solution of 4.2 g. (0.009 mol) 3,4-dimethyl-7-{3-[4-(4-nitrobenzamido)-piperidino]-propoxy}-coumarin in 100 ml. methanol and 100 ml. tetrahydrofuran is hydrogenated at ambient temperature and 1 bar hydrogen pressure over 1 ml. Raney nickel. The reaction mixture is then filtered, the filter is washed with methylene chloride and methanol, the filtrate is evaporated and the residue is recrystallized from methanol. There are obtained 2.8 g. (71% of theory) 7-{3-[4-(4-aminobenzamido)-piperidino]-propoxy}-3,4-dimethyl-coumarin; m.p. 242°–245° C.

EXAMPLE 13

7-[3-(4-Benzamido-piperidino)-propoxy]-3-n-butyl-4-methylcoumarin 4.65 g. (0.02 mol) 7-Hydroxy-3-n-butyl-4-methyl-coumarin are mixed with 6.18 g. (0.022 mol) 3-(4-benzamido-piperidino)-propyl chloride and 5.53 g. (0.04 mol) potassium carbonate in 50 ml. dimethylformamide. After stirring the reaction mixture for 4 hours at 100° C., followed by cooling, the desired compound precipitates out and is recrystallized from ethanol. There are obtained 5.4 g. (58.6% of theory) 7-[3-(4-benzamido-piperidino)-propoxy]-3-n-butyl-4-methyl-coumarin; m.p. 170°–171° C. From the concentrated filtrate, by means of column chromatography (silica gel/methylene chloride-methanol 9:1 v/v), there are obtained a further 2 g. of pure product.

EXAMPLE 14

In a manner analogous to that described in Example 13, there are obtained:

| | designation | Yield % | m.p. °C. (solvent) |
|---|---|---|---|
| (a) | 7-{3-[4-(4-Fluorobenzamido)-piperidino]-propoxy}-3-n-butyl-4-methyl-coumarin from 7-hydroxy-3-n-butyl-4-methyl-coumarin and 3-[4-(4-fluoro-benzamido)-piperidino]-propyl chloride | 53 | 185–186 (ethanol) |
| (b) | 7-[3-(4-Benzamido-piperidino)-propoxy]-4-methyl-8-n-propyl-coumarin from 7-hydroxy-4-methyl-8-n-propyl-coumarin and 3-(4-benzamido-piperidino)-propyl chloride | 49 | 177–178 (ethanol) |
| (c) | 7-{3-[4-(4-Fluorobenzamido)-piperidino]-propoxy}-4-methyl-8-n-propyl-coumarin from 7-hydroxy-4-methyl-8-n-propyl-coumarin and 3-[4-(4-fluoro-benzamido)-piperidino]-propyl chloride | 68 | 176–177 (ethanol) |
| (d) | 7-[3-(4-Benzamido-piperidino)-propoxy]-3,4-dimethyl-8-n-propyl-coumarin from 7-hydroxy-3,4-dimethyl-8-n-propyl-coumarin and 3-(4-benzamido-piperidino)-propyl chloride | 54 | 190–191 (ethanol) |
| (e) | 7-{3-[4-(4-Fluorobenzamido)-piperidino]-propoxy}-3,4-dimethyl-8-n-propyl-coumarin from 7-hydroxy-3,4-dimethyl-8-n-propyl-coumarin and 3-[4-(4-fluorobenz-amido)-piperidino]-propyl chloride | 51 | 206–207 (ethanol) |
| (f) | 7-[3-(4-Benzamido-piperidino)-propoxy]-3-n-butyl-4-methyl-8-n-propyl-coumarin from 7-hydroxy-3-n-butyl-4-methyl-8-n-propyl-coumarin and 3-(4-benz-amido-piperidino)-propyl chloride | 62 | 117–118 column chromatography CH$_2$Cl$_2$/methanol |
| (g) | 7-{3-[4-(4-Fluorobenzamido)-piperidino]-propoxy}-3-n-butyl-4-methyl-8-n-propyl-coumarin from 7-hydroxy-3-n-butyl-4-methyl-8-n-propyl-coumarin and 3-[4-(4-fluorobenzamido)-piperidino]-propyl chloride | >50 | 169–170 (ethanol) |
| (h) | 7-[3-(4-Benzamido-piperidino)-propoxy]-4,8-dimethyl-coumarin from 7-hydroxy-4,8-dimethyl-coumarin and 3-(4-benzamido-piperidino)-propyl chloride | 63 | 183–184 (ethanol) |
| (i) | 7-[3-(4-Benzamido-piperidino)-propoxy]-3,4,8-trimethyl-coumarin from 7-hydroxy-3,4,8-trimethyl-coumarin and 3-(4-benzamido-piperidino)-propyl chloride | 68 | 206 |
| (j) | 7-[3-(4-Benzamido-piperidino)-propoxy]-4-methyl-8-acetyl-coumarin from 7-hydroxy-4-methyl-8-acetyl-coumarin and 3-(4-benzamido-piperidino)-propyl chloride | 74 | 208–209 (ethanol) |
| (k) | 7-[3-(4-Benzamido-piperidino)-propoxy]-3,4-dimethyl-8-acetyl-coumarin from 7-hydroxy-3,4-dimethyl-8-acetyl-coumarin and 3-(4-benzamido-piperidino)-propyl chloride | 67 | 207–208 (ethanol) |
| (l) | 7-[3-(4-Benzamido-piperidino)-propoxy]-4-methyl-5-hydroxy- | 58 | amorphous |

| designation | Yield % | m.p. °C. (solvent) |
|---|---|---|
| coumarin from 5,7-dihydroxy-4-methyl-coumarin and 3-(4-benzamido-piperidino)-propyl chloride | | |
| (m) 7-[3-(4-Benzamido-piperidino)-propoxy]-4-methyl-5-methoxy-coumarin (a) from compound 14(1) by methylation, or (b) from 5-methoxy-7-hydroxy-4-methyl-coumarin and 3-(4-benzamido-piperidino)-propyl chloride | 55 | amorphous |
| (n) 7-{3-[4-(4-Fluorobenzamido)-piperidino]-propoxy}-4-methyl-5-hydroxy-coumarin from 4-methyl-5,7-dihydroxy-coumarin and 3-[4-(4-fluorobenzamido)-piperidino]-propyl chloride | | |
| (o) 7-[3-(4-Benzamido-piperidino)-propoxy]-4,5-dimethyl-coumarin from 4,5-dimethyl-7-hydroxy-coumarin and 3-(4-benzamido-piperidino)-propyl chloride | 88 | 175–176 |
| (p) 7-[3-(4-Benzamido-piperidino)-propoxy]-3,4,5-trimethyl-coumarin from 3,4,5-trimethyl-7-hydroxy-coumarin and 3-(4-benzamido-piperidino)-propyl chloride | 61 | 193–194 $CH_2Cl_2$/ diethyl ether |

The foregoing compounds can be used as such or they can be converted to salts with pharmacologically acceptable acids. They can be administered orally, as pills, tablets, capsules, powders and the like. The preferred form of oral administration is a tablet containing 10 to 300 mg of active compound.

The compounds can also be administered parenterally. Injection solutions containing 50 mg/ml of injection solution are preferred.

With respect to the proper dosage and methods of application for the instant compounds, these are comparable to those for the commercially known compound "Fragivix", i.e. 2-ethyl-3-(4'-hydroxybenzoyl)-benzofuran. The instant compounds make possible comprehensive therapy of acute as well as chronic phlebological and capillary afflictions as well as varicose syndromes. The instant compounds retard reactions leading to edemas and swellings, including those of allergic origin.

The typical daily dosage of 10 to 300 mg results in reducing or eliminating the above afflictions, commonly within some days. A preferred dosage is 30–100 mg.

EXAMPLE 15

Tablets are produced, each tablet containing 10 mg. 7-[3-(4-benzamido-piperidino)-propoxy]-3,4-dimethyl-coumarin. The tablets are prepared according to the following formulation:

| 7-[3-(4-benzamido-piperidino)-propoxy]-3,4-dimethylcoumarin | 10 g. |
|---|---|
| lactose | 80 g. |
| starch | 29 g. |
| magnesium stearate | 1 g. |

The coumarin derivative is finely powdered and mixed with the lactose and starch, whereafter the mixture is granulated in conventional manner. The magnesium stearate is added to the granulate and the mixture pressed to give 1000 tablets, each with a weight of 0.12 g.

The superior activity of the novel compounds is shown by comparing the inhibition of the passive cutaneous anaphylactic reaction in rats produced by injection of serum containing reaginic antibodies to egg albumin. Diethylcarbamazin, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of *Bordetellapertussis* vaccine (Behring: $2 \times 10^{10}$ organisms/ml) 9–14 Days later the animals were bled from the abdominal aorta; the serum was pooled and stored at −20° C. until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at 56° C. for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans Blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

The test material was injected intravenously immediately before the antigen, using a solution in water containing 0.5% HCl and 2% of dimethylformamide. For comparative purposes there was also tested diethylcarbamoyl-4-methylpiperazine sold under the tradename Diethylcarbamazin. The volumes of the injections were varied to give the indicated dosage of the active material. The results obtained were as follows:

Homologous PCA reaction in rats induced by reaginic antibodies (Ovalbumin (2×cryst.) and *Bord. pertussis* ($2 \times 10^{10}$); Application of the Compounds: p.o. 40 min before Ovalbumin, 6 rats/dose and 6 controls.

TABLE

| Compounds | p.o. dose (mg/kg) | % Inhibition of PCA |
|---|---|---|
| Diethylcarbamazin | 100.0 | 47 |
| Example 1 | 3.0 | 50 |
| Example 2a | 3.0 | 59 |
| Example 2b | 3.0 | 36 |
| Example 2d | 3.0 | 52 |
| Example 4a | 3.0 | 61 |
| Example 6 | 3.0 | 30 |

TABLE-continued

| Compounds | p.o. dose (mg/kg) | % Inhibition of PCA |
|---|---|---|
| Example 7b | 3.0 | 23 |
| Example 8 | 3.0 | 34 |
| Example 10 | 3.0 | 54 |

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What we claim is:

1. An aryl ether derivative of the formula

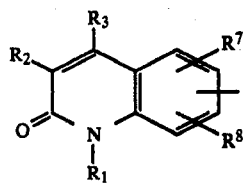

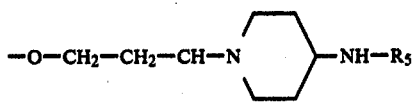

wherein
$R_1$ is a hydrogen atom or a lower alkyl radical,
$R_2$ and $R_3$ each independently is a hydrogen atom or lower alkyl radical,
$R_5$ is a hydrogen atom or a lower alkanoyl radical optionally substituted by halogen, aryl or benzthiazole derivatives; a lower alkenoyl radical optionally substituted by aryl; an aroyl, furancarbonyl, thiophenecarbonyl or pyridinecarbonyl radical optionally substituted by halogen, hydroxyl, lower alkyl, lower alkoxy, lower alkoxycarbonyl, lower alkanoyloxy, carboxyl, nitro, amino, nitrile, trifluoromethyl, carbamoyl or benzyl; a $C_{3-7}$-cycloalkylcarboxylic acid radical, a benzenesulphonic acid radical; or a lower alkyl sulphonic acid radical,
$R_7$ is a hydrogen atom, a lower alkyl radical or a lower alkanoyl radical, and
$R_8$ is a hydrogen atom, a lower alkyl radical, a lower alkoxy radical or a hydroxyl group;
or a pharmacologically acceptable salt thereof.

2. A compound according to claim 1, wherein said compound is 6-[3-(4-benzamido-piperidino)-propoxy]-1,4-dimethyl-2-oxo-1,2-dihydroquinoline of the formula

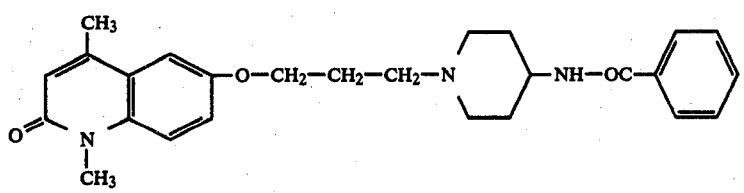

or a pharmacologically acceptable salt thereof.

3. An anti-allergic composition of matter comprising an anti-allergically effective amount of a compound or salt according to claim 1 in admixture with a diluent.

4. A method of combating an allergic response in a patient which comprises administering to the patient an antiallergically effective amount of a compound or salt according to claim 1.

5. The method according to claim 4, in which the material administered is
6-[3-(4-benzamido-piperidino)-propoxy]-1,4-dimethyl-2-oxo-1,2-dihydroquinoline,
or a pharmacologically acceptable salt thereof.

* * * * *